(12) United States Patent
Kadambi

(10) Patent No.: US 7,341,350 B1
(45) Date of Patent: Mar. 11, 2008

(54) METHOD FOR EVALUATING AND MEASURING ACCOMMODATION AMPLITUDE AND RANGE AND A DEVICE FOR EMPLOYING SAME

(75) Inventor: Vivek Kadambi, Bangulory (IN)

(73) Assignee: Kadambi Brothers, LLC, Fort Wayne, IN (US)

( * ) Notice: Subject to any disclaimer, the term of this patent is extended or adjusted under 35 U.S.C. 154(b) by 596 days.

(21) Appl. No.: 10/771,745

(22) Filed: Feb. 4, 2004

Related U.S. Application Data (60) Provisional application No. 60/445,554, filed on Feb. 6, 2003.

(51) Int. Cl.
*A61B 3/00* (2006.01)
(52) U.S. Cl. .................................. 351/245; 351/246
(58) Field of Classification Search ................ 351/200, 351/222, 244–246, 239
See application file for complete search history.

(56) References Cited

U.S. PATENT DOCUMENTS 2,523,007 A * 9/1950 Glazer ........................ 351/239

* cited by examiner

*Primary Examiner*—Alicia M Harrington
(74) *Attorney, Agent, or Firm*—Kreig DeVault LLP (57) ABSTRACT

A method for evaluating and measuring accommodation amplitude in one or both eyes of a person by subjecting the person to a near-vision visual acuity test comprising a target having optotypes displayed thereon, different targets having different sized optotypes, determining the nearest point at which the person accurately identifies a majority of the optotypes on the target, and introducing either a sufficiently powered plus lens or sufficiently powered minus lens to locate the nearest point within an identified range of distances from the eye. An apparatus is also disclosed for employing the versions of the method, comprising a holder connected to a slide rule, a track for movably positioning the holder, and a lens positioner for introducing plus or minus lenses as needed. A reference point marker may be positioned along the track for identifying the range of distances at which the nearest point is desired to be located.

39 Claims, 10 Drawing Sheets

METHOD FOR EVALUATING AND MEASURING ACCOMMODATION AMPLITUDE AND RANGE AND A DEVICE FOR EMPLOYING SAME

This application claims priority based on U.S. Provisional Patent Application Ser. No. 60/445,554, entitled "Method for Evaluating and Measuring Accommodation Amplitude and Range and a Device for Employing Same," and filed Feb. 6, 2003.

DETAILED DESCRIPTION OF VERSIONS OF THE INVENTION

Although the disclosure hereof is detailed and exact in order to enable those skilled in the art to practice the invention, the physical versions herein disclosed merely exemplify the invention which may be embodied in other specific structure. The scope of the invention is defined in the claims appended hereto.

Illustrated in the drawings and disclosed herein are versions of a method 10 for evaluating and measuring accommodation amplitude and range in one or both eyes 12 of a person 14.

Accommodation generally is the adjustment to the lens 16 within the eye 12 to focus on objects located at various near and far distances from the eye 12. Accommodation is typically measured in diopters (D), an arbitrary measure of the power of refraction. A lens having a dioptric (refractive) power of 1 D brings rays of light to a focus point 1 meter from the source of the rays. Similarly, a lens having a power of 2 D brings rays of light to a focus point ½ meter from the source of the rays, and a lens having a power of ½ D brings rays of light to a focus point 2 meters from the source of the rays. In an eye 12, the light rays emitted from an image are focused on the retina 18, which remains a generally fixed and negligible distance from the surface of the lens 16 within the eye 12.

In order to properly focus images on the retina 18, the lens 16 of the eye 12 must be adjusted in shape in order to refocus accordingly when the image is near versus when the image is far. Accommodation amplitude ("AA") is the highest dioptric power of the lens 16 of the eye 12 that is physically achievable. This is generally achieved when a properly focused image is at the nearest point 20 relative to the eye 12 while maintaining proper focus. AA generally varies from person to person.

AA is measured and evaluated according to the versions of the method 10 by determining the nearest point 20 of focus by a person 14 on a target 22 such that the nearest point 20 is located within a predetermined range 24 of distances 26 from the eye 12, and introducing a sufficiently powered additional lens 28 in front of the eye 12 to ensure that such location is within the predetermined range 24. In one version, a person's eye 12 is evaluated without any distance vision correction in place, i.e. without glasses, contacts, or other corrective lenses via a phoropter or lens trial frame in place to assist the person's general distance vision. In other versions, the person's eye 12 is evaluated using full distance vision correction of some kind in place.

AA is generally calculated by the formula (AA)=100/(distance 26 in centimeters between the target 22 and the eye 12 at the actual nearest point 20). This may also be referred to as the "gross" AA. According to the versions of the present invention, AA is calculated by the formula (AA)=100/(distance 26 in centimeters between the target 22 and the eye 12 at the nearest point 20)−(dioptric power of a plus or minus lens 30, 32 placed in front of the eye 12 to locate the nearest point 20 within the predetermined range 24). This value represents the "net" AA at the nearest point 20 located within the predetermined range 24. In one version, full distance vision correction is in place during evaluation. In other versions, the right side of the formula for net AA further subtracts the dioptric power of the vision correction that is in place. In yet other versions, net AA is calculated without accounting for the dioptric power of the vision correction.

It is common practice in the industry to measure AA with the person's full distance vision correction in place during examination, but to determine the net AA without subtracting the power of such correction. Similarly, if AA is measured without such correction in place, net AA, according to industry practice, may be determined by subtracting what the correction should have been. For example, if for an eye with −5.0 D myopia the person 14 wears the full correction (−5.0 D eyeglass lens) and measures a net AA, according to the present invention, of 2.3 D, the final value is 2.3 D. If, however, the examination is performed without the −5.0 D distance correction in place, the value of AA measured according to the present invention will be about 7.3 D, but the −5.0 D is "added back" to this value to arrive at the net AA of 2.3 D, conforming to the common industry practice. As a result, net AA, according to use of the present invention in conformance with common practices, is the gross AA measurement plus the power of an additional lens 28 required to locate the nearest point 20 within the predetermined range 24. It will be appreciated, however, that net AA may be determined by also subtracting the power of corrective lenses if circumstances dictate or industry practices are adjusted or otherwise changed.

The general formula for measuring net AA above is derived from the rule that lens powers are additive. That is, placing a 1 D lens generally adjacent a 3 D lens will provide an overall lens power of 4 D. According to versions of the invention, at the nearest point 20, the lens 16 of the eye 12 has its strongest physically achievable dioptric power because the shorter the distance 26 an image has to become focused to a point, the stronger the power of the overall lens required to achieve the focus. If 1 D is the focusing power for an image at 1 meter (100 centimeters), then the total power of the overall lens at the eye 12 (i.e. the lens 16 of the eye 12 plus any corrective lens plus any additional lens 28 to locate the nearest point 20 within the predetermined range 24) equals 100 divided by the distance 26 in centimeters between the target 22 and the eye 12. The accommodative power of the lens 16 of the eye 12 is thus the overall lens power at that nearest point 20 minus the powers of any other lenses in the overall lens, such as the additional lens 28.

Figure 16:
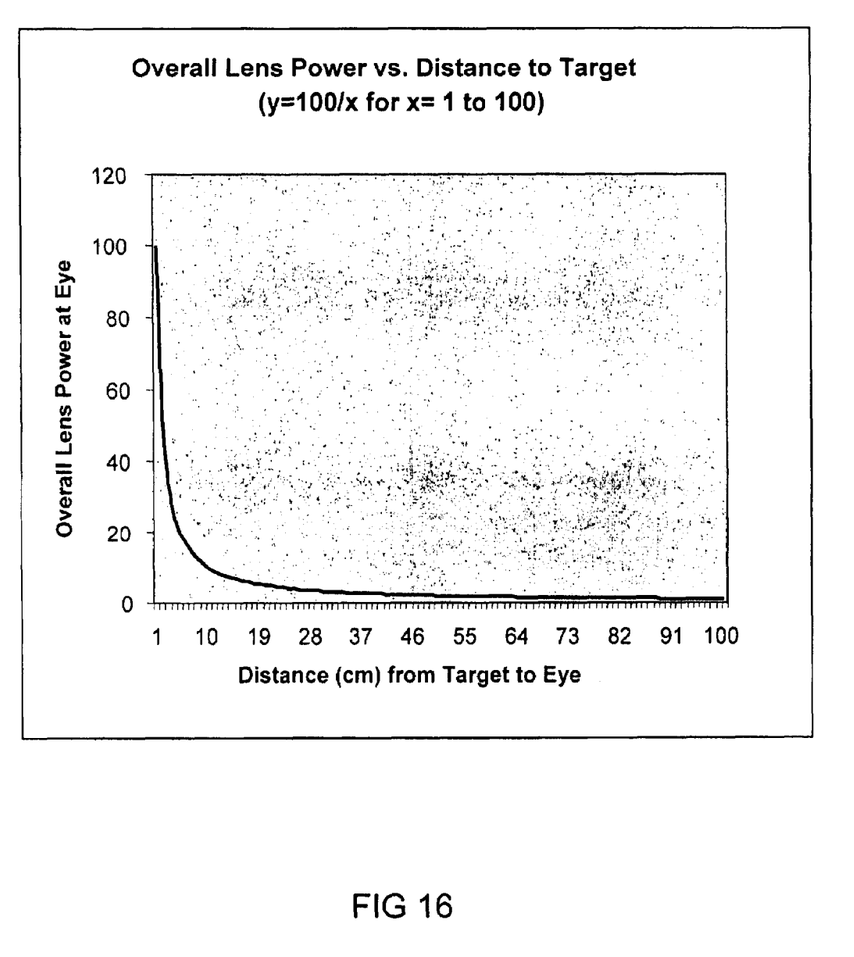

AA is evaluated according to versions of the present invention by locating the nearest point 20 within a limited predetermined range 24 of distances 26 from the eye 12 for which a change in distance 26 within the range 24 causes a relatively constant change in the eye's accommodation power. To focus on a target 22 at any distance 26, the dioptric power of the overall lens (i.e. the accommodated power of the lens 16 of the eye 12 plus the power of any additional lens 28) equals (100)/(distance 26 in centimeters between the target 22 and the eye 12). Refer to FIG. 16 for the relationship of overall lens power to distance 26 between the target 22 and the eye 12. This, thus, is an inverse relationship, for which only limited ranges in the most common near-vision distance values (10 centimeters to 60 centimeters) have a relatively constant affect on accommodation.

In one version, the nearest point 20 (also referred to generally as the "near point", "blur point" and "point of blur" and referring generally to the point of commencement of blurring of optotypes 34 on a target 22 as the target 22 is brought closer to the eye 12) is located within a predetermined range 24 of distances 26 from the eye 12 for which the dioptric power of the overall lens is within a range at which a change in distance 26 results in a relatively constant change in dioptric power of the overall lens. In other versions, the predetermined range 24 of potential nearest point 20 locations has a length of between about 10 centimeters and about 50 centimeters. In yet other versions, the predetermined range 24 of potential nearest point 20 locations has a length of between about 15 centimeters and about 25 centimeters. In yet other versions, the predetermined range 24 of potential nearest point 20 locations has a length of about 20 centimeters. In yet other versions, the nearest point 20 is to be located between about 20 centimeters and about 40 centimeters from the eye 12 of the person 14.

Figure 1:
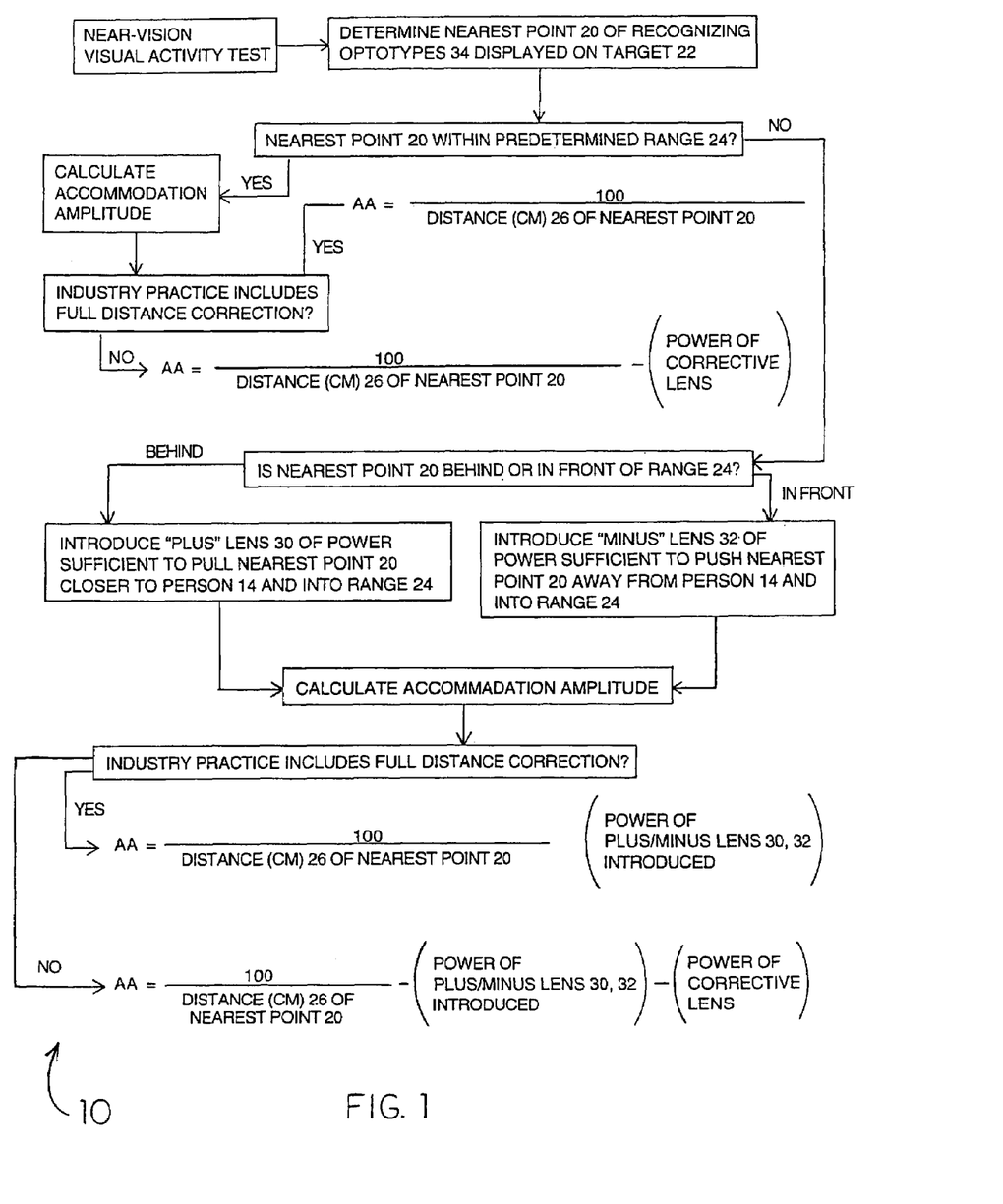
FIG. 1 shows a flow diagram illustrating steps of evaluating accommodation amplitude according to versions of the invention.
Figure 2:
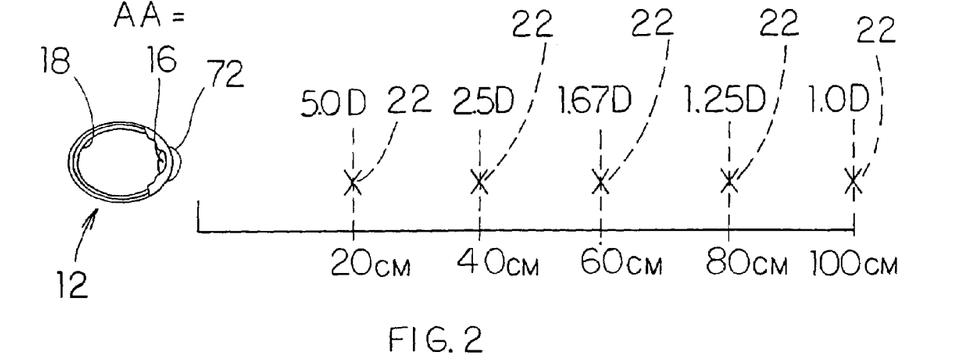
FIG. 2 is an illustration of the effect on the dioptric power of accommodation of the lens of the eye reviewing targets at various distances.
Figure 3:
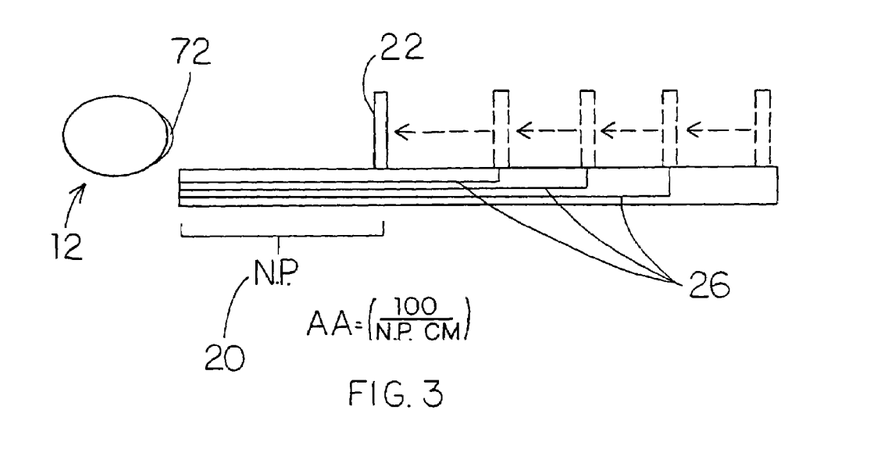
FIG. 3 shows evaluation of accommodation amplitude according to prior art methods.
Figure 4:
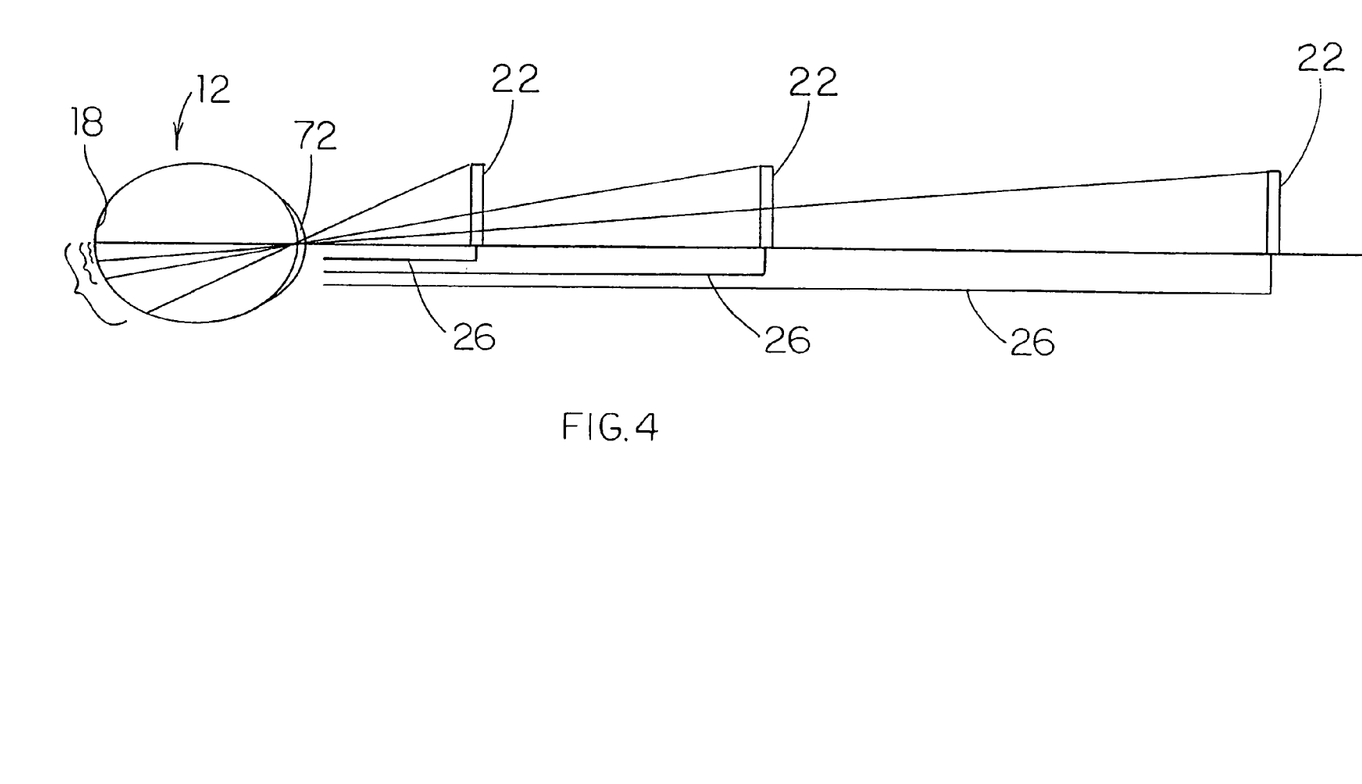
FIG. 4 shows the effect of change of distance of a target on retinal image size, i.e. the magnification effect.
Figure 5:
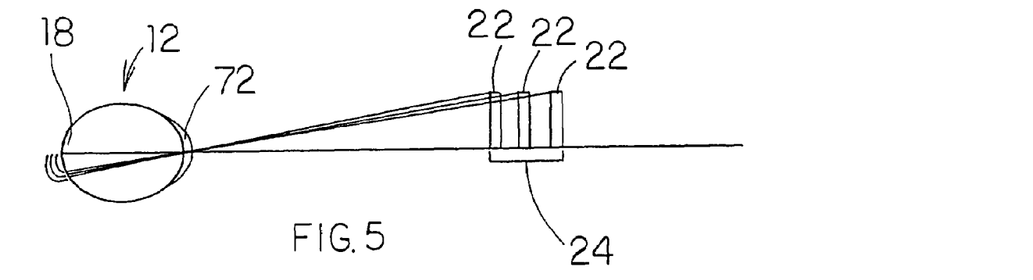
FIG. 5 shows a restricted range of distance variation that minimizes the magnification effect.

In addition to considering the foregoing factors for identifying a desirable predetermined range 24, an evaluator 36 using versions of the method 10 may also consider the effect of magnification that occurs when a target's 22 distance 26 from the eye 12 varies greatly. As shown in FIG. 4, the image of the target 22 focused on the retina 18 of the eye 12 is magnified when the target 22 is relatively near, and is minimized when the target 22 is moved further away. The magnification effect, according to versions of the invention, is considered in identifying the predetermined range 24, and dictates a restricted such range, as shown in FIG. 5, that avoids artificially aiding a person 14 due to magnified target image that assists focusing on optotypes 34 to resist blurring.

In order to locate the nearest point 20 within the predetermined range 24, evaluation of AA is first performed without any additional lens 28. (As discussed above, distance vision correction may be used during this evaluation, and is differentiated from any additional lens 28 used to relocate the nearest point 20 to within the predetermined range 24.) If the nearest point 20 located in this way is outside the predetermined range 24, an additional lens 28 is introduced in front of the eye 12 as needed to adjust the location of the nearest point 20, which adjustment is accomplished by inducing further accommodation of the lens 16 of the eye 12. If the nearest point 20 is located in front of the predetermined range 24, a "minus" lens 32 is introduced to push the nearest point 20 away from the person 14. If the nearest point 20 is located beyond the predetermined range 24, a "plus" lens 30 is introduced to pull the nearest point 20 closer to the person 14. In one version, such plus or minus lenses 30, 32 are introduced by trial and error until the nearest point 20 is located as desired. In other versions, the appropriate plus or minus lens 30, 32 is estimated on the basis of the out-of-range location of the nearest point 20 and the estimated degree of adjustment required to locate the nearest point 20 within the range 24.

Figure 6:
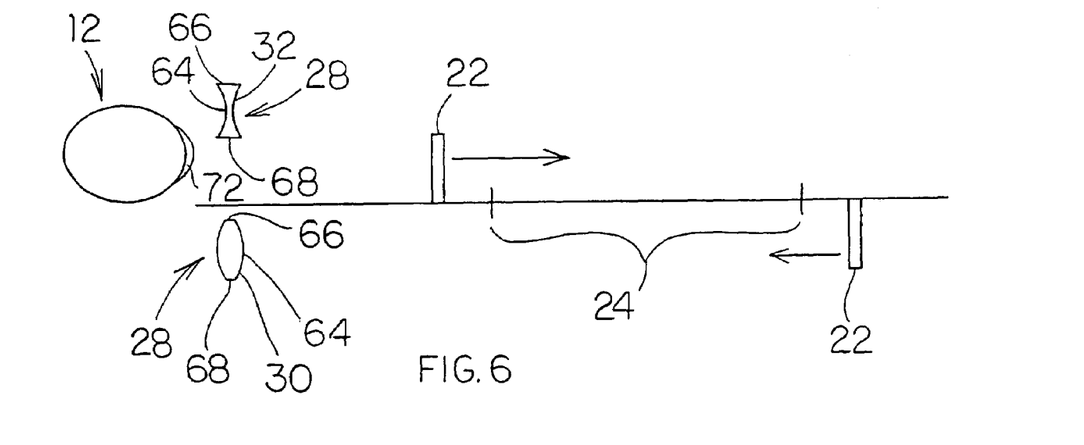
FIG. 6 illustrates the effect of a plus or minus lens on the location of the nearest point according to versions of the present invention.

As shown in FIG. 6, a plus lens 30 generally comprises a convex lens, i.e. a lens thicker in the middle 64 than at the upper and lower ends 66, 68 of the lens in side profile. Such a lens 30 has a "positive" dioptric power. It also has a slight magnification effect that is negligible for purposes hereof for powers up to +3 D. Conversely, a minus lens 32 generally comprises a concave lens, i.e. a lens thinner in the middle 64 than at the upper and lower ends 66, 68 of the lens in side profile. Such a lens 32 has a "negative" dioptric power. It also has a slight minification effect that is negligible for purposes hereof for powers down to −3 D. Obviously, whether the dioptric power of a lens (either a corrective lens or an additional lens introduced during evaluation) is positive or negative has direct bearing on the dioptric power of the overall lens. Thus, the nearest point 20 may be determined within the predetermined range 24 using such additional lenses 28. In one version, the predetermined range 24 is selected so that plus lenses 30 used in this regard have a power of 3 D or less. In other versions, minus lenses 32 used in this regard have a power of −3 D or less. The range 24 of locations of nearest points 20 determined using more than one plus or minus lens 30, 32 may be recorded as needed.

AA can be calculated at any position of the target 22 within the predetermined range 24 once the nearest point 20 is known. The accommodative power of the overall lens may be calculated once the distance 26 between the eye and the target 22 at the near point 20 is known.

In one version, the steps for determining the location of the nearest point 20 comprise subjecting the person 14 to a basic near-vision visual acuity test. Such a test may be any recognized or ad hoc test for determining near-vision visual acuity. In other versions, the target 22 in any such test comprises one or more optotypes 34 (testing images) displayed thereon, as shown in FIGS. 12A-12D. In yet other versions, various targets 22 may be selectively used, each target 22 having optotypes 34 of different sizes than optotypes displayed on other targets. In the latter version, evaluation of AA is performed using at least two different targets 22, such as in FIGS. 12B and 12C.

In one version, recognized visual acuity tests are employed. One recognized near-vision visual acuity test comprises a card having the Snellen Test printed thereon (not shown). The Snellen Test is generally known for testing distance vision by placing a Snellen Test chart on a wall and requiring the person to recognize letters on the chart from a distance. In one version of the present invention, the Snellen Test is produced on a card and size-adjusted for near-vision acuity testing and used accordingly for determining the location of the nearest point.

Figure 12A:
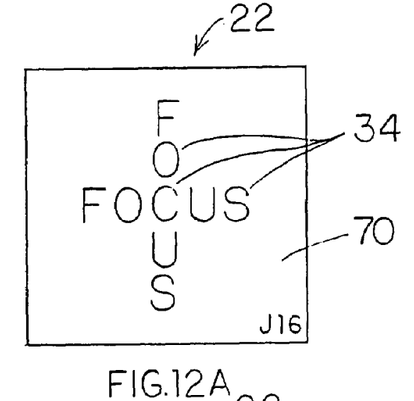
FIG. 12A illustrates one version of a target displaying relatively large optotypes.
Figure 12B:
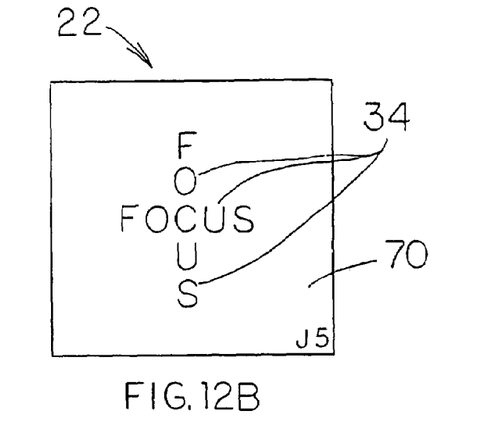
FIG. 12B illustrates another version of a target displaying optotypes smaller than on the target of FIG. 12A.
Figure 12C:
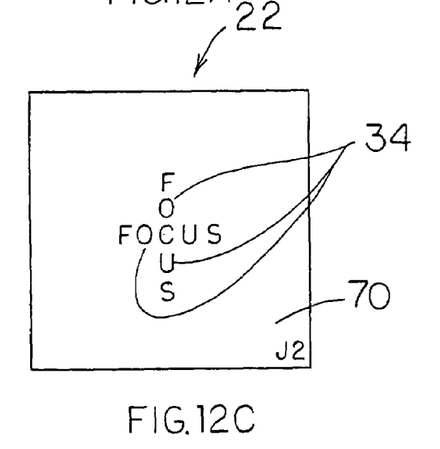
FIG. 12C illustrates another version of a target displaying optotypes smaller than on the target of FIG. 12B.
Figure 12D:
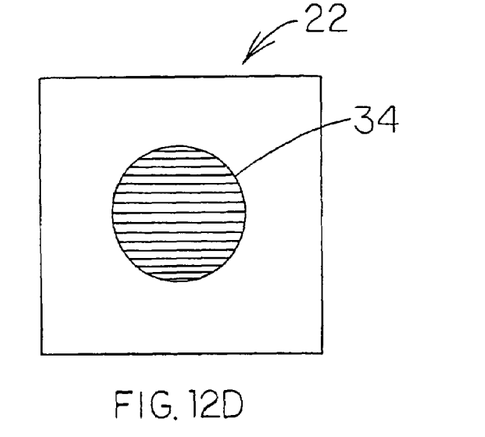
FIG. 12D illustrates another version of a target displaying a design as the optotypes.

Another recognized near-vision visual acuity test is the Jaeger Test. Referring now to FIGS. 12A-12C, the Jaeger Test generally comprises a plurality of cards 70 having writing displayed thereon, each card 70 having optotypes 34 of a particular size. For example, card J1 has the smallest optotype size and card J16 has the largest optotype size. In one version of the present invention, one or more cards 70 from the Jaeger Test is used for determining the location of the nearest point 20. In other versions, the cards J16, J5 and J2 are used for determining the location of the nearest point 20 for each of those cards 70. Other cards 70 with larger or smaller optotypes 34 may be used according to the visual acuity of the person 14. In yet other versions, the card J16 is used to familiarize the person 14 in the performance of the AA evaluation method 10 disclosed herein, and cards J5 and J2 are used for taking actual AA measurements in the performance of the AA evaluation method 10 disclosed herein.

In one version, two sizes of optotypes 34 are used and up to two differently powered additional lenses 28 are used to relocate nearest point 20 within the predetermined range 24. The average reading is then taken after eliminating extreme or skewed readings. The final reading is the determination with the smallest sized optotype 34 such as the card J2 in the Jaeger Test. In other versions, if the person 14 is unable to give reliable readings with the card J2, then the card J5, for example, with larger optotypes 34, may be used to indicate the final reading. In yet other versions, the optotype size is referenced in the notes, reports or other documentation (not shown) regarding the AA reading, such as in parentheses, so that the reading of AA may be subjected to correct interpretation by those of ordinary skill in the art and/or those reasonably familiar with the types of cards 70 and optotypes 34 of different visual acuity tests.

In operation, versions of the present invention comprise one or more of the following steps: a person 14 having AA in one or both eyes 12 evaluated is subjected to a near-vision visual acuity test. In one version, the target 22 from such test has generally universally recognizable optotypes 34 of a particular size. The target 22 is positioned in the line of sight of a single eye 12 being tested or parallel to and generally equidistant between the lines of sight of both eyes 12 for a binocular evaluation. The target 22 is gradually moved at an unhurried rate from a distant position to a closer position relative to the eye or eyes 12 until the target 22 reaches the nearest point 20 at which the person 14 initially experiences blurring while viewing the optotypes 34 on the target 22. In one version, the target 22 is moved closer to the eye 12 beyond the nearest point 20 to overshoot it and demonstrate to the person 14 and/or exaggerate the blurring of optotypes 34, then the target 22 is pulled away to make the optotypes 34 clear again, then closer to the point of blur (nearest point) 20. This may be repeated in back and forth movement of the target 22 until reasonable preciseness of the nearest point 20 is determined.

In the event that the nearest point 20 so determined is outside a predetermined range 24 as desired by the evaluator 36, an additional plus lens 30 or minus lens 32 is introduced in front of the eye or eyes 12 as needed, such lens 28 having a dioptric power sufficient to locate the nearest point 20 to within the predetermined range 24. The predetermined range 24 is identified in accordance with the above disclosure. A minus lens 32 of sufficient dioptric power is used to push the nearest point 20 away from the eye or eyes 12, and a plus lens 30 of sufficient dioptric power is used to pull the nearest point 20 closer to the eye or eyes 12. Once the nearest point 20 is located within the predetermined range 24 of distances 26 from the eye 12 and its relatively precise location is determined for purposes of the evaluation, the net AA is calculated according to the formula (AA)=100/(distance 26 in centimeters of the target 22 from the eye(s) 12 at the nearest point 20)−(dioptric power of any plus or minus lens 30, 32). As discussed above, in one version, full distance vision correction is placed in front of the eye or eyes 12, such as eyeglasses, contacts, a phoropter, or eyeglasses trial frame (not shown). In other versions, and depending on common industry practices regarding determination of AA, the formula is adjusted accordingly to account for such correction, namely (AA)=100/(distance 26 in centimeters of the target 22 from the eye(s) 12 at the nearest point 20)−(dioptric power of any plus or minus lens 30, 32)+(deficit in dioptric power of the full distance vision correction).

The dioptric power exhibited by a lens 28 introduced in front of the eye(s) 12 in operation is actually slightly lower than the actual dioptric power listed for such lens 28. This is as a result of the slight distance between the introduced lens and the cornea 72 of the eye 12. Thus, the more accurate power of any added plus or minus lens 30, 32 in the overall lens evaluated is the "corneal power" of such lens 30, 32. The corneal power ("CP") of any additional lens 28 may be calculated according to the formula (CP)=(listed dioptric power of the added plus or minus lens 30, 32)/(1−(d*(listed dioptric power of the added plus or minus lens 30, 32))), where d equals the distance in meters that the added plus or minus lens 30, 32 is located in front of the cornea 72 of the person's eye 12. In one version, the value of d is generally presumed to be about 0.013 meters. However, in light of the relatively small value of d and its minimal (and arguably negligible) corrective effect on the actual dioptric power of the added plus or minus lens 30, 32, other versions of the present invention do not use the CP of the introduced lens 28 but rather the actual dioptric power thereof.

Figure 12E:
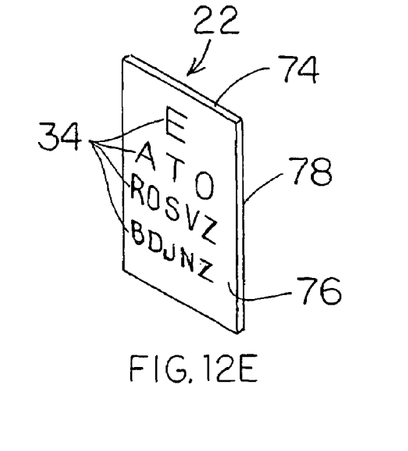
FIG. 12E illustrates a version of a target comprising a one-way mirror for use in versions of the present invention employing an objective accommodation measuring device.
Figure 12F:
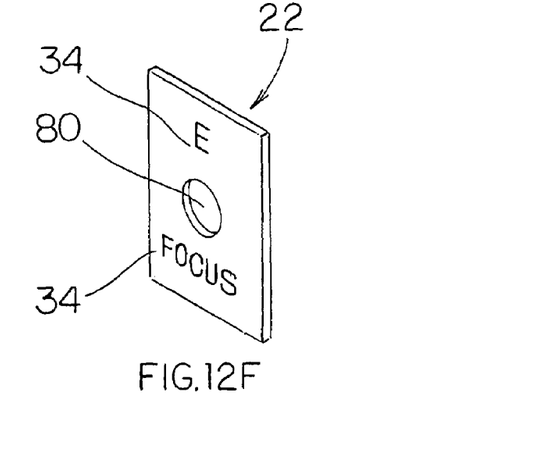
FIG. 12F illustrates a version of an alternative target for use in versions of the present invention employing an objective accommodation measuring device.
Figure 13:
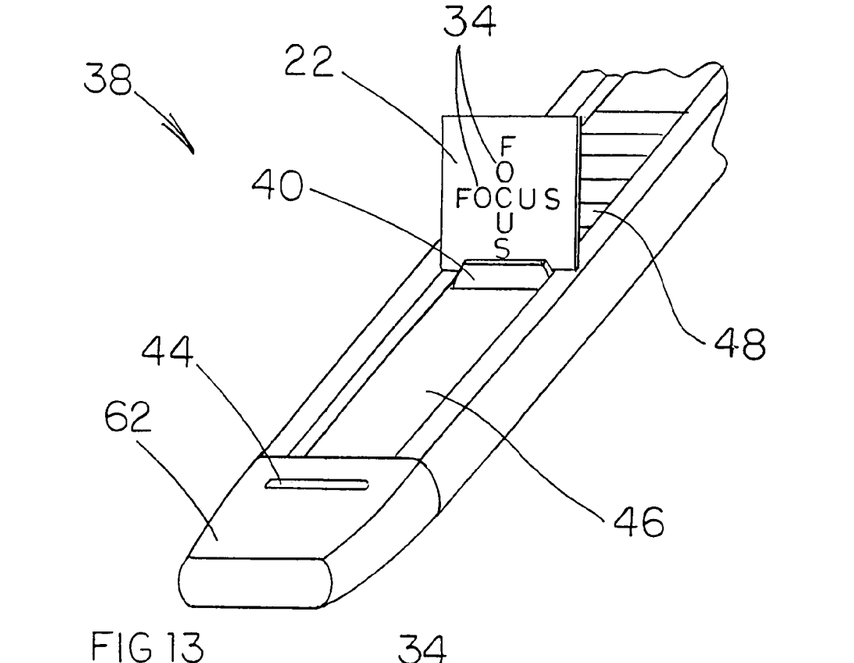
FIG. 13 illustrates a perspective view of the apparatus of FIG. 10 having a target positioned in the holder.

In other versions of the present invention, an objective accommodation measuring device (not shown) positioned oppositely facing the eye(s) 12 being evaluated is used to measure AA in conjunction with versions of the disclosed method. In one such version, the objective accommodation measuring device comprises a dynamic retinoscopy machine. In other versions, such a device measures AA in the line of sight of the eye 12 being tested by measuring through the target 22. In one such version shown in FIG. 12E, the target 22 comprises a one-way mirror 74 having a mirror side 76 and a viewer side 78, the viewer side 78 being opposite the mirror side 76, the optotypes 34 being displayed on the mirror side 76 in the person's view. The objective measuring device then measures AA through the viewer side 78 of the one-way mirror 74. In other such versions as shown in FIG. 12F, the target 22 comprises an aperture 80 extending therethrough, located generally centrally in the target 22. The objective measuring device thus measures AA through the aperture 80.

Table 1 shows results of measured AA in several exemplary test subjects on whom versions of the method 10 of the present invention were performed. The evaluations were conducted under standard conditions. The near-vision visual acuity test comprised the Jaeger Test, using cards J16, J5 and J2. The predetermined range 24 was identified to be 20 centimeters long and having a nearest point 20 distance range of between 20 centimeters and 40 centimeters from each test subject's eye 12 on the basis of the relatively straight line relationship of overall lens power between 20 cm and 40 cm (overall power=5 D at 20 cm and 2.5 D at 40 cm).

TABLE 1

| Test Subject | Nearest Point | Overall Lens Power | Correction Power | Additional Lens Power | Measured AA |
|---|---|---|---|---|---|
| #1 | 31.25 cm | 3.2 | 0 | 1.0 | 2.2 |
| #2 | 23.26 cm | 4.3 | 0 | 2.0 | 2.3 |
| #3 | 32.26 cm | 3.1 | 0 | 2.0 | 1.1 |
| #4 | 23.81 cm | 4.2 | 0 | 3.0 | 1.2 |

Various apparatuses 38 may be employed for performing the various versions of the method 10 disclosed herein and for measuring AA. Such apparatuses 38 generally have means for presenting a target 22 to the person 14 at varying distances 26. In one version, such means comprise a track-and-slide arrangement 82 for moving a target 22 nearer and farther from the eye 12. In other versions, such means comprise an optical system (not shown) displaying a virtual image of the target. Such an optical system may comprise an arrangement of mirrors or a screen display of computer or micro-processor generated images.

Figure 14:
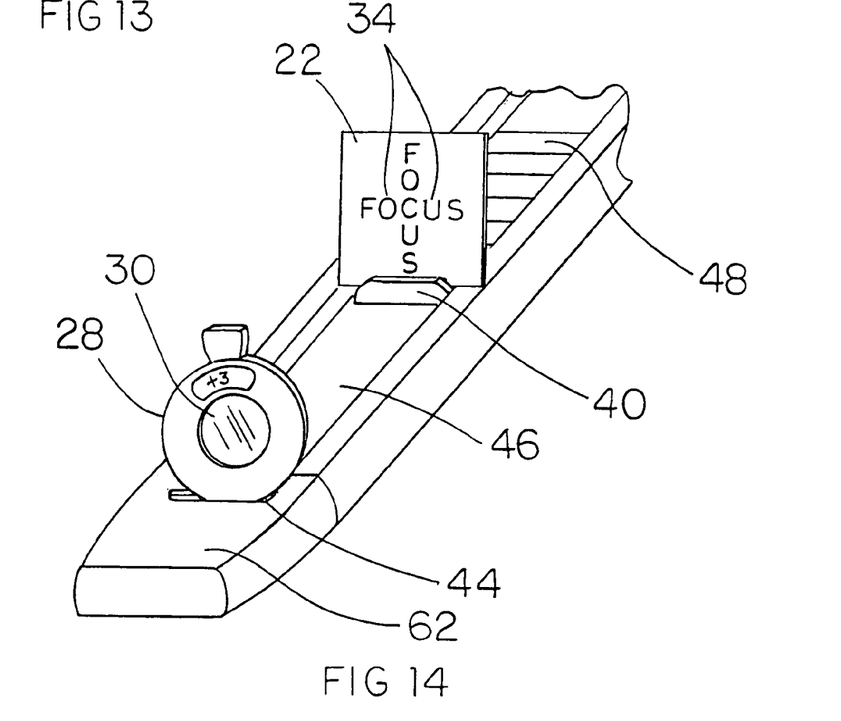
FIG. 14 illustrates a perspective view of the apparatus of FIG. 13 further having a plus lens within the lens positioner.
Figure 15:
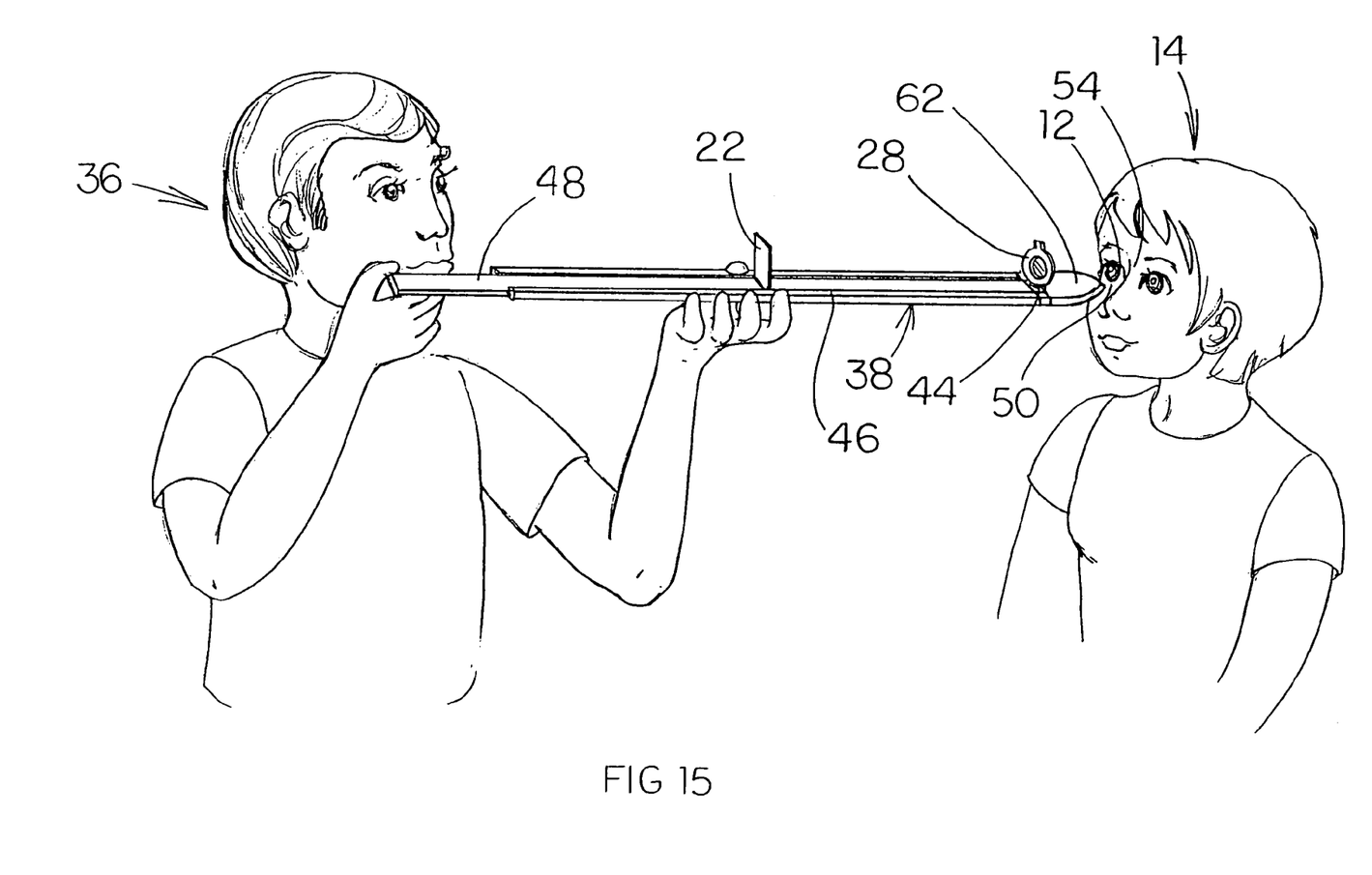
FIG. 15 illustrates a person having accommodation amplitude for one eye evaluated according to the versions of the present invention.

Versions of an apparatus 38 comprising a track-and-slide arrangement 82 are shown in FIGS. 8-11 and 13-15. In one version, the apparatus 38 comprises a holder 40, a slide rule or vernier 42, and a lens positioner 44. The slide rule or vernier 42 comprises a track 46 and a control piece 48. In one such version, the control piece 48 slideably engages the track 46 coaxially so that the control piece 48 is slideably movable the length of the track 46. In another such version, the control piece 48 threadedly engages the track 46 coaxially so that the control piece 48 is threadedly movable the length of the track 46. The holder 40 is connected to one end 84 of the control piece 48 and is movable relative to the track 46 by pushing or pulling the control piece 48 having a slideable engagement, or, for threaded engagements, turning the control piece 48 clockwise or counterclockwise relative the track 46 to screw or unscrew the threaded engagement. The holder 40 is configured to receive the target 22 used for the evaluation. The lens positioner 44 is provided at the end 62 of the apparatus 38 which is mounted adjacent the eye 12 being evaluated. The lens positioner 44 is configured to receive a lens 28 introduced for adjusting the location of the nearest point 20 to within the predetermined range 24 of distances 26 from the eye 12, as shown in FIG. 14.

In one version, the apparatus 38 is mounted adjacent the eye 12 of the person 14, for example at the inferior orbital margin 50 of the eye 12. So mounted, the track 46 and control piece 48 are substantially aligned with the line of sight for the eye 12. In other versions, the apparatus 38 further comprises a bridge piece 52 removably secured to the end 62 of the apparatus for mounting the apparatus 38 adjacent the bridge 54 of the person's nose between the person's eyes 12. In such versions, the apparatus 38 is employed for binocular evaluation of AA, and the track 46 and control piece 48 are aligned substantially parallel to and equidistant between the lines of sight for each of the person's eyes 12. A control piece 48 will be moved gradually toward the eye 12. In one version, this movement is relatively slow, at an unhurried rate, generally less than about 2 cm per second.

In versions shown in FIGS. 8-14, the apparatus 88 further comprises a plurality of distance markings 56 displayed along the track 46 or on the control piece 48. The markings 56 indicate relative distances 26 of target 22 from a person's eye 12 when the apparatus 38 is appropriately mounted adjacent the eye 12. In one version shown in FIG. 8, the apparatus 38 further comprises a reference point marker 58 that is movably mounted adjacent the track 46. In such versions, the marker 58 has a length generally consistent with the length of the predetermined range 24 for locating the nearest point 20. In one such version, the marker 58 is mounted adjacent the track 46 to indicate distances 26 within which to locate the nearest point 20 as between about 10 centimeters and about 60 centimeters from the eye 12. In other such versions, the length of the marker 58 is from about 10 centimeters long to about 50 centimeters long. In yet other such versions, the marker 58 is from about 15 centimeters long to about 25 centimeters long. In yet other such versions, the marker 58 is about 20 centimeters long. In yet other such versions, the marker 58 is mounted adjacent the track 46 in order to locate the nearest point 20 between about 20 centimeters from the eye 12 and about 40 centimeters from the eye 12. By fixing the target 22 in position or minimizing the movement of the target 22 from about 15 centimeters to about 40 centimeters and using lenses 28 in front of the eye 12 to find the point of blur which corresponds to the nearest point 20, the effect of magnification and minification of the retinal image during evaluation is mitigated.

Figure 10:
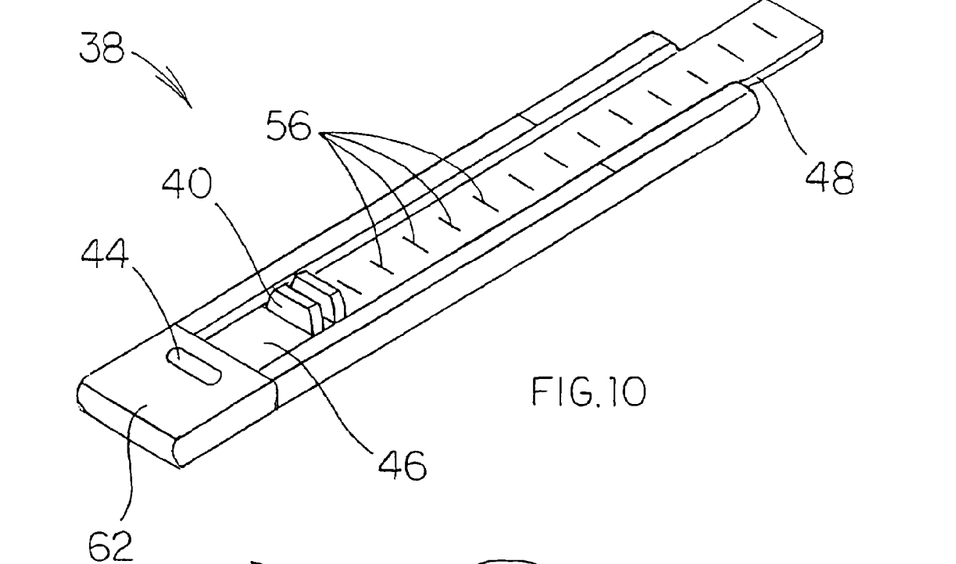
FIG. 10 is a perspective view of another version of an apparatus for evaluating accommodation amplitude according to the versions of the disclosed method.
Figure 11:
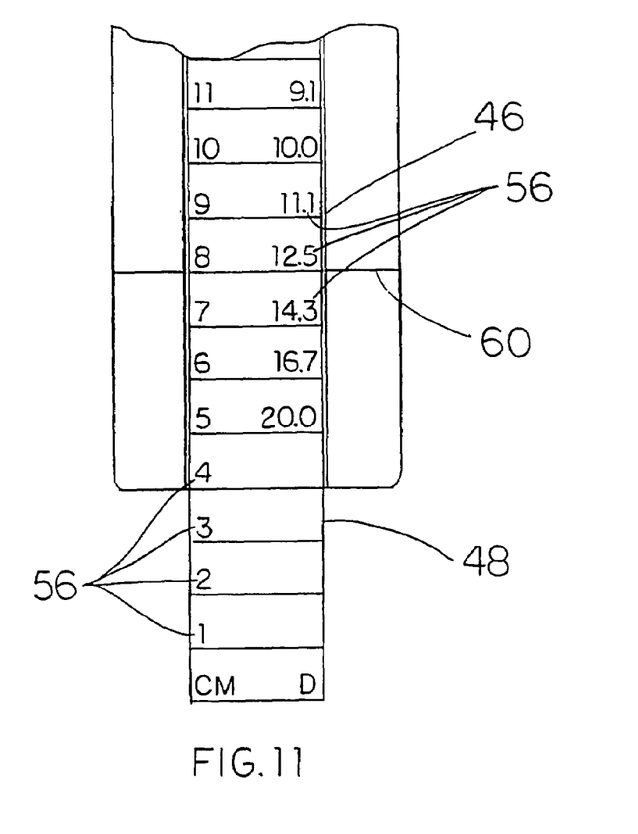
FIG. 11 is a top view of the back end of the apparatus of FIG. 10 showing distance and power markings on the control piece.

In versions shown in FIGS. 10 and 11, a reference mark 60 is provided along the track 46 and markings 56 are provided on the control piece 48 that indicate. the distance 26 between a person's eye 12 and the holder 40. The markings 56 are calibrated to display this distance 26 at the reference mark 60. As shown in FIG. 11, the dioptric power of the gross AA, calculated according to the formula (AA) =100/distance (cm), is also displayed in the markings 56 relative to a particular distance 26. In versions of the method 10 disclosed above, the calculating step is deemed to be performed also by taking readings from an apparatus 38 that indicates the gross AA at various nearest points 20 and subtracting the power of a plus or minus lens 30, 32, if any.

In one version of the apparatus 38, movement of the control piece 48 may be provided mechanically and/or manually. In other versions, the distance 28 may be determined electronically within the apparatus 38 and displayed on an LCD or other appropriate digital display screen (not shown) mounted on the apparatus 38. In yet other versions, the gross AA is electronically determined and displayed on such a screen (not shown).

Figure 7:
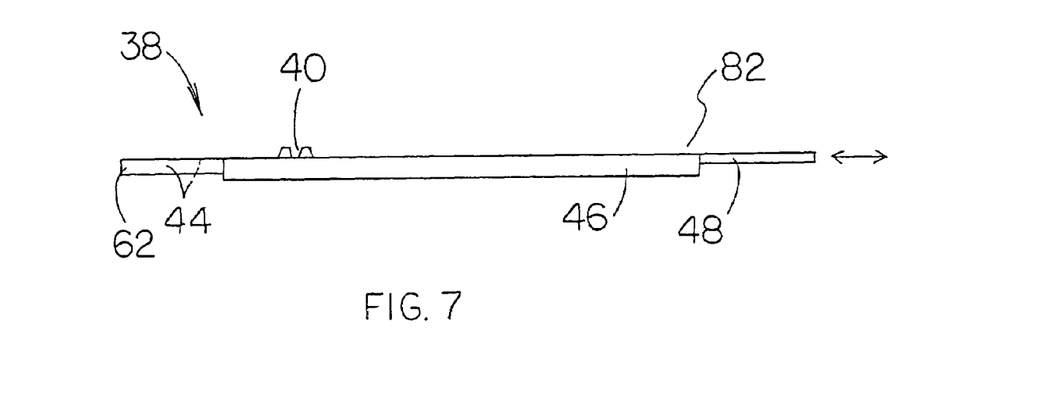
FIG. 7 illustrates a side view of one version of an apparatus for evaluating accommodation amplitude according to various versions of the present invention.
Figure 8:
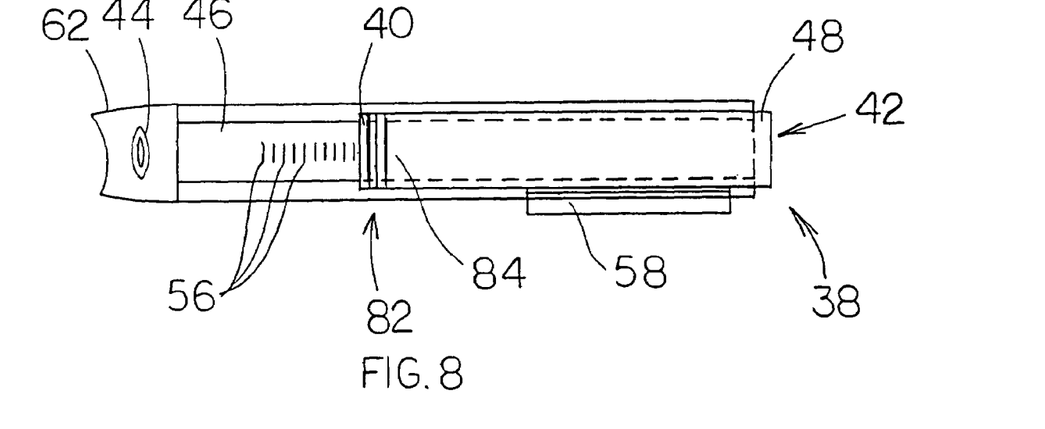
FIG. 8 illustrates a top view of another version of the apparatus of FIG. 7.
Figure 9:
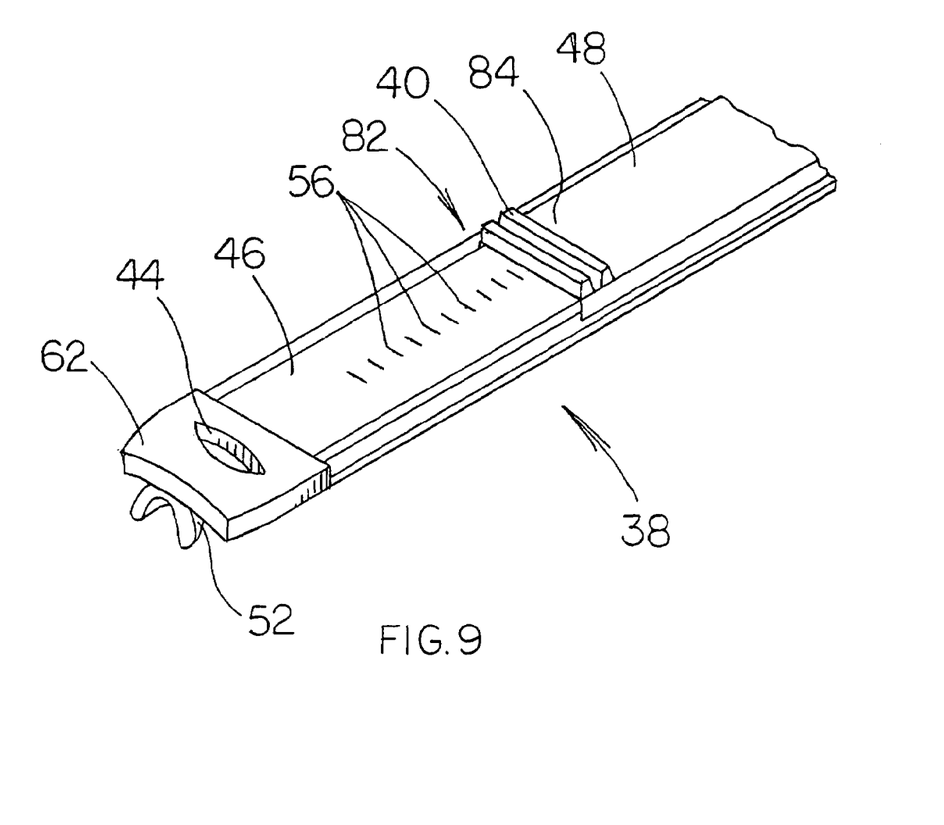
FIG. 9 illustrates a perspective view of the apparatus shown in FIG. 8 further comprising a bridging piece.

The apparatuses 38 shown in FIGS. 7-9 may have a mounting end 62 configured for mounting directly adjacent the eye 12, such as by placing the end 62 against the inferior orbital margin 50 of the eye 12. In other versions, the mounting end 62 is configured for mounting the apparatus 38 on a phoropter (not shown) used in connection with the versions of the method 10 disclosed herein.

In other versions, AA as well as the range of accommodation may be evaluated and measured. In such versions, rather than moving the target 22 in order to find a nearest point 20 located within the predetermined range 24, the target 22 is fixed in a position within the predetermined range 24, and a series of plus and/or minus lenses 30, 32 are introduced in front of the eye 12 to determine the range of powers of such added plus and/or minus lenses 30, 32 for which the person 14 can recognize the optotypes 34 displayed on the target 22. As a result of determining such a range, one may also determine the range of accommodation of the lens 16 of the eye 12 that is physically achievable because the lens 16 of the eye 12 will have adjusted from its highest power to its weakest power. In determining accommodation range, in one version the concern is with the range of the lens 16 of the eye 12 alone. For such evaluations, the power of the distance vision correction in place is subtracted from the gross accommodation.

For example, if the target 22 is fixed a distance 26 of 20 centimeters from the eye 12, the power of the overall lens (the gross accommodation), as described above, is 5D. Assuming no distance vision correction is needed for the person 14, the accommodation power of the lens 16 of the eye 12 is 5 D. By introducing lenses 28 in front of the eye 12 having powers between −5 D and 15 D and subjecting the person 14 to the near-vision visual acuity test, visual acuity is evaluated for powers of the overall lens between 0 D (no refraction at all) and 20D. Without refraction by the overall lens, the person 14 will not be able to recognize the optotypes 34. The power of the lens 28 introduced in front of the eye 12 for which the person 14 can first recognize optotypes 34 on the target 22 is generally the equivalent of the lens used to adjust the nearest point 20 to within the predetermined range 24, as described above. Thus, AA is measured for an "equivalent" nearest point 20 of 20 centimeters by subtracting the power of the introduced lens 28 from 5 D.

By continuing the progression through the series of lenses 28 up to 15 D, at some point the person 14 will no longer be able to recognize the optotypes 34 on the target 22. The stronger the dioptric introduced lens 28, the weaker the dioptric power of the lens 16 of the eye 12. When the person 14 can no longer recognize the optotypes 34 at 20 centimeters, the weakest power that the lens 16 of the eye 12 can physically achieve has been reached, and may be calculated using the same formula provided for calculating AA, wherein AA instead equals the weakest physically achievable power of the lens 16 of the eye 12. Thus, the range of accommodation of the lens 16 of the eye 12 is determined.

An apparatus 38, including any apparatus disclosed herein, that is suitable for the moving target method disclosed above may also be employed for evaluating AA and range of accommodation pursuant to the stationary target method described above.

While specific versions of the invention have been shown and described herein for purposes of illustration, the protection offered by any patent which may issue upon this application is not strictly limited to the disclosed versions; but rather extends to all structures, steps and arrangements which fall fairly within the scope of the claims which are appended hereto:

What is claimed is:

1. A method for evaluating accommodation amplitude in an eye of a person comprising the steps of: subjecting said person to a near-vision visual acuity test, said test comprising at least one target having a plurality of optotypes displayed thereon, said optotypes on one said target having a different size than optotypes on another of said targets; determining a nearest point at which said person initially experiences blurring while viewing said optotypes on each said target; introducing one of a plus lens or a minus lens in front of said eye of said person as needed and having a dioptric power sufficient to locate said nearest point to within a predetermined range of distances from said eye, said minus lens of sufficient dioptric power being used to push said nearest point further away from said eye and into said range as needed, said plus lens of sufficient dioptric power being used to pull said nearest point closer to said eye and into said range as needed; and calculating said accommodation amplitude from a formula comprising (AA)=100/(distance in centimeters between said target and said eye at said nearest point)−(dioptric power of said plus or minus lens).

2. The method of claim 1 wherein said range is from about 10 centimeters long to about 50 centimeters long.

3. The method of claim 2 wherein said range is from about 15 centimeters long to about 25 centimeters long.

4. The method of claim 1 wherein said range is about 20 centimeters long and corresponds to locating said nearest point a distance from said eye of between about 20 centimeters and about 40 centimeters.

5. The method of claim 1 wherein said test is the Jaeger Test, each said target comprising a card having typed writing displayed thereon.

6. The method of claim 5 wherein said card is chosen from the group of cards consisting of card J16, card J5 and card J2.

7. The method of claim 6 wherein using said J16 card comprises training said person in the performance of said method, and using said J5 card and said J2 card comprises evaluating said accommodation amplitude, a final determination of said accommodation amplitude being made either by an average reading from evaluations from said J5 card and said J2 card or by a reading from evaluation from said J2 card.

8. The method of claim 1 wherein binocular accommodation amplitude is evaluated by subjecting both eyes of said person simultaneously to said test.

9. The method of claim 1 wherein said test is performed on said person having full distance vision correction in place, said full distance vision correction being selected from the group of vision correction devices consisting of eyeglasses, contacts, a phoropter, and an eyeglasses trial frame.

10. The method of claim 9 wherein said formula comprises (AA)=100/(distance in centimeters of said target from said eye at said nearest point)−(dioptric power of said plus or minus lens)+(deficit in dioptric power of said full distance vision correction).

11. The method of claim 1 wherein said dioptric power of said plus or minus lens in said formula comprises the corneal power of said plus or minus lens, said corneal power being calculated according to the formula (Corneal Power)=(listed dioptric power of said plus or minus lens)/(1−(d*(listed dioptric power of said plus or minus lens))), wherein d=the distance in meters that said one of said plus lens or said minus lens is located in front of the cornea of said eye.

12. The method of claim 11 wherein the value of d is presumed to be about 0.013 meters.

13. An apparatus for evaluating accommodation amplitude comprising: a holder, a track, a control piece, and a lens positioner, said holder configured to holdably receive a target, said control piece engaging said track coaxially in a manner of engagement selected from the group consisting of slidably and threadedly, said holder connected to an end of said control piece and movable relative to said track by manipulation of the engagement of said control piece with said track, said lens positioner configured to receive one of a plus lens or a minus lens, said apparatus being mounted at one end adjacent an eye of a person, said track being aligned with the line of sight for said eye.

14. The apparatus of claim 13 further comprising a plurality of distance markings displayed along said track indicating relative distances from said eye when said apparatus is mounted adjacent said eye.

15. The apparatus of claim 14 further comprising a reference point marker movably mounted adjacent said track, said marker having a length consistent with a predetermined range for locating a near point within distances from said eye as desired, said marker being positioned along said track for indicating said distances.

16. The apparatus of claim 15 wherein said marker is positioned to indicate said distances within which to locate said near point as between about 10 centimeters and about 60 centimeters from said eye.

17. The apparatus of claim 15 wherein said predetermined range is from about 10 centimeters long to about 50 centimeters long.

18. The apparatus of claim 15 wherein said predetermined range is from about 15 centimeters long to about 25 centimeters long.

19. The apparatus of claim 15 wherein said predetermined range is about 20 centimeters long, said marker being positioned to locate said near point as between about 20 centimeters and about 40 centimeters from said eye.

20. The apparatus of claim 13 wherein said one end is configured for mounting said apparatus on a phoropter.

21. The apparatus of claim 13 further comprising a bridge piece removably secured to said one end for mounting said apparatus adjacent said person's nose bridge between said eye and the other eye of said person, said track being aligned substantially parallel and equidistant between the lines of sight for each of said eyes.

22. A method for evaluating accommodation amplitude and range of accommodation in an eye of a person comprising the steps of: subjecting said person to a near-vision visual acuity test, said test comprising at least one target having a plurality of optotypes displayed thereon, said optotypes on one said target having a different size than optotypes on another of said targets; fixing said target in a position that is a known distance from said eye regardless of whether said person can accurately identify any optotypes on said target; introducing a series of lenses, said lenses graduating or diminishing within a spectrum of dioptric power; noting the dioptric power of each said lens for which said person can accurately identify a majority of said optotypes on said target; and calculating said accommodation amplitude from a first formula comprising (AA)=(100)/(distance in centimeters between said position and said eye)−(lowest dioptric power of a said lens for which said person can accurately identify a majority of said optotypes on said target).

23. The method of claim 22 further comprising calculating the strongest physically achievable accommodation of said eye from a second formula comprising (strongest accommodation)=(100)/(distance in centimeters between said position and said eye)−(highest dioptric power of a said lens for which said person can accurately identify a majority of said optotypes on said target).

24. The method of claim 23 wherein said position is a distance of about 20 centimeters from said eye.

25. The method of claim 23 wherein said spectrum is from about −5 D to about 15 D.

26. The method of claim 23 wherein said test is the Jaeger Test, each said target comprising a card having typed writing displayed thereon.

27. The method of claim 23 wherein said test is the Jaeger Test, each said target comprising a card having typed writing displayed thereon, and said card is chosen from the group of cards consisting of card J16, card J5 and card J2.

28. The method of claim 23 wherein said test is the Jaeger Test, each said target comprising a card having typed writing displayed thereon, and said card is chosen from the group of cards consisting of card J16, card J5 and card J2, and wherein using said J16 card comprises training said person in the performance of said method, and using said J5 card and said J2 card comprises evaluating said accommodation amplitude and said range of accommodation.

29. The method of claim 23 wherein binocular accommodation amplitude is evaluated by subjecting both eyes of said person simultaneously to said test.

30. The method of claim 23 wherein said test is performed on said person having full distance vision correction in place, said full distance vision correction being selected from the group of vision correction devices consisting of eyeglasses, contacts, a phoropter, and an eyeglasses trial frame.

31. The method of claim 23 wherein said test is performed on said person having full distance vision correction in place, said first formula comprises (AA)=(100)/(distance in centimeters between said position and said eye)−(lowest dioptric power of a said lens for which said person can accurately identify a majority of said optotypes on said target)+(deficit in dioptric power of said full distance vision correction), and said second formula comprises (weakest accommodation)=(100)/(distance in centimeters between said position and said eye)−(lowest dioptric power of a said lens for which said person can accurately identify a majority of said optotypes on said target)+(deficit in dioptric power of said full distance vision correction).

32. The method of claim 22 wherein said position is a distance of about 20 centimeters from said eye.

33. The method of claim 22 wherein said spectrum is from about −5 D to about 15 D.

34. The method of claim 22 wherein said test is the Jaeger Test, each said target comprising a card having typed writing displayed thereon.

35. The method of claim 22 wherein said test is the Jaeger Test, each said target comprising a card having typed writing displayed thereon, and said card is chosen from the group of cards consisting of card J16, card J5 and card J2.

36. The method of claim 22 wherein said test is the Jaeger Test, each said target comprising a card having typed writing displayed thereon, and said card is chosen from the group of cards consisting of card J16, card J5 and card J2, and wherein using said J16 card comprises training said person in the performance of said method, and using said J5 card and said J2 card comprises evaluating said accommodation amplitude.

37. The method of claim 22 wherein binocular accommodation amplitude is evaluated by subjecting both eyes of said person simultaneously to said test.

38. The method of claim 22 wherein said test is performed on said person having full distance vision correction in place, said full distance vision correction being selected from the group of vision correction devices consisting of eyeglasses, contacts, a phoropter, and an eyeglasses trial frame.

39. The method of claim 22 wherein said test is performed on said person having full distance vision correction in place, and said first formula comprises (AA)=(100)/(distance in centimeters between said position and said eye)−(lowest dioptric power of a said lens for which said person can accurately identify a majority of said optotypes on said target)+(deficit in dioptric power of said full distance vision correction).

* * * * *